United States Patent [19]

Cocco

[11] Patent Number: 4,814,498

[45] Date of Patent: Mar. 21, 1989

[54] SEPARATION/PURIFICATION OF PARA-HYDROXYBENZOIC ACID

[75] Inventor: Roger Cocco, Saint-Symphorien D'Ozon, France

[73] Assignee: Rhone-Poulenc Specialites Chimiques, Courbevoie, France

[21] Appl. No.: 924,427

[22] Filed: Oct. 29, 1986

[30] Foreign Application Priority Data

Oct. 29, 1985 [FR] France .................. 85 16260

[51] Int. Cl.$^4$ .............................................. C07C 65/01
[52] U.S. Cl. .................................................. 562/475
[58] Field of Search ........................................ 562/475

[56] References Cited

FOREIGN PATENT DOCUMENTS

| | | | |
|---|---|---|---|
| 1061806 | 12/1953 | France . | |
| 1539528 | 9/1968 | France . | |
| 8072147 | 9/1973 | Japan ................................. | 562/475 |
| 728511 | 4/1955 | United Kingdom . | |
| 1167095 | 10/1969 | United Kingdom . | |

*Primary Examiner*—Paul J. Killos
*Attorney, Agent, or Firm*—Burns, Doane, Swecker & Mathis

[57] ABSTRACT

Essentially pure para-hydroxybenzoic acid crystals, typically containing but trace amounts of inorganic potassium salts and salicylic or 4-hydroxyisophthalic acid, well adopted for foodgrade applications, are facilely recovered from an aqueous solution of dipotassium and/or monopotassium para-hydroxybenzoate by (i) adding an organic solvent for para-hydroxybenzoic acid to such aqueous solution, in an amount sufficient to dissolve the para-hydroxybenzoic acid corresponding to said potassium salts thereof, (ii) next adding thereto an at least stoichiometric amount, relative to said dipotassium and/or monopotassium salt of para-hydroxybenzoic acid, and (iii) separating therefrom an essentially organic phase which comprises said para-hydroxybenzoic acid and an aqueous phase which comprises an inorganic potassium salt.

12 Claims, No Drawings

SEPARATION/PURIFICATION OF PARA-HYDROXYBENZOIC ACID

CROSS-REFERENCE TO RELATED APPLICATION

Copending application, Ser. No. 924,424 filed concurrently herewith and assigned to the assignee hereof.

BACKGROUND OF THE INVENTION

1. Field of the Invention

The present invention relates to the separation and purification of para-hydroxybenzoic acid, and, more especially, to the precipitation of para-hydroxybenzoic acid from its dipotassium and/or monopotassium salt and to the purification thereof.

2. Description of the Prior Art

The dipotassium and/or monopotassium salt of para-hydroxybenzoic acid may be prepared, notably, by the carboxylation of potassium phenate with carbon dioxide. The reaction is generally carried out under a pressure of a few bars (2 to 10 bars) and at a temperature on the order of 200° C.

Typically, the phenate is carboxylated in the presence of free phenol and the reaction is carried out in a dispersant liquid medium. Compare, for example, French patents Nos. 1,564,997 and 2,065,098.

Upon completion of the reaction, the reaction mass is treated in order to separate therefrom the potassium salts of hydroxybenzoic and hydroxyphthalic acids obtained, in this case principally dipotassium and/or the monopotassium salt of para-hydroxybenzoic acid and, in much smaller proportions, potassium salicylate and potassium 4-hydroxyisophthalate.

This treatment may especially include addition of water, which dissolves the potassium salts of hydroxybenzoic and hydroxyphthalic acids, and a liquid/liquid extraction step using a water-immiscible solvent. Such an operation thus provides an organic solution containing, in particular, free phenol and an aqueous solution containing the potassium salts mentioned above.

Serious need exists in this art for the improved precipitation and purification of para-hydroxybenzoic acid from such aqueous solutions.

Indeed, the treatment of aqueous solutions of the dipotassium and/or the monopotassium salt of para-hydroxybenzoic acid typically includes precipitating parahydroxybenzoic acid and the other organic acids with a strong inorganic acid, and especially with sulfuric acid. This treatment requires a large excess of the strong inorganic acid and several successive washings with water to remove the maximum of the inorganic salt formed (most frequently, potassium sulfate). The para-hydroxybenzoic acid obtained can then be crystallized once, or several times, in order to reduce the level of other organic acids contained therein.

The para-hydroxybenzoic acid obtained by the usual process contains amounts of potassium sulfate, and to a lesser extent, salicylic acid and 4-hydroxyisophthalic acid, which are still too high for certain applications of para-hydroxybenzoic acid in the food industry.

SUMMARY OF THE INVENTION

Accordingly, a major object of the present invention is the provision of an improved process for the separation/purification of para-hydroxybenzoic acid, which improved process enables the simple production of parahydroxybenzoic acid of sufficient purity for common end uses, or the production of para-hydroxybenzoic acid of very high purity, also be way of a process far simpler than those of the prior art.

Briefly, the present invention features a process for the precipitation and purification of para-hydroxybenzoic acid from an aqueous solution of the dipotassium and/or the monopotassium salt of para-hydroxybenzoic acid, comprising the following sequence of stages:

1. addition thereto of an organic solvent for para-hydroxybenzoic acid, in an amount sufficient to dissolve the para-hydroxybenzoic acid corresponding to the potassium salts in such aqueous solution;

2. addition of a strong inorganic acid in an amount at least equal to the stoichiometric amount relative to the dipotassium and/or monopotassium salt of parahydroxybenzoic acid;

3. separation of an essentially organic phase containing para-hydroxybenzoic acid and of an aqueous phase containing the inorganic potassium salt formed.

DETAILED DESCRIPTION OF THE PREFERRED EMBODIMENTS OF THE INVENTION

More particularly according to the present invention, any acid capable of releasing para-hydroxybenzoic acid from its dipotassium and/or monopotassium salt can be used as the strong inorganic acid; sulfuric acid, hydrochloric acid and phosphoric acid are representative. Because of cost or lower corrosion factors, it is generally preferred to use sulfuric acid.

In the description of the process of the invention that follows, acidification by sulfuric acid will threfore be more frequently referred to for convenience, but this does not exclude use of other strong inorganic acids.

The organic solvents which are suitable for carrying out the process according to the invention are solvents in which the para-hydroxybenzoic acid is soluble, whereas potassium sulfate is insoluble, or only slightly soluble.

Representative are aliphatic ethers, substituted aliphatic ethers, aliphatic ketones, halogenated aliphatic ketones, aliphatic aldehydes, and aliphatic alcohols.

For practical and economic reasons, it is not desirable to use organic solvents which have a very high boiling point, as the solvent will generally be removed by distillation during the isolation of para-hydroxybenzoic acid and, upon completion of purification, the para-hydroxybenzoic acid must contain the least possible trace amounts of the solvent used.

Thus, a solvent having a boiling point less than or equal to 120° C. and, even more particularly, less than or equal to 100° C., will be preferred.

Exemplary of such solvents, the following are representative:

aliphatic ethers, such as diisopropyl ether;
methyl tert-butyl ether; ethyl isopropyl ether; ethyl propyl ether; butyl ethyl ether; ethyl isobutyl ether; ethyl tert-butyl ether; butyl methyl ether; isobutyl methyl ether; methyl pentyl ether; diethyl ether; dipropyl ether; isopropyl propyl ether; ethyl 1-propynyl ether; ethyl 2-propynyl ether; ethynyl propyl ether; allyl ethyl ether; allyl isopropyl ether; isopropyl vinyl ether or isobutyl vinyl ether;
halogenated aliphatic ethers, such as 2-bromoethyl ethyl ether; 2-chloroethyl ethyl ether;

aliphatic ketones, such as acetone; 2-butanone; 3-methyl-2-butanone; 3,3-dimethyl-2-butanone; 2-pentanone or 3-pentanone;

chlorinated aliphatic ketones, such as 3-chloro-2butanone or 1-chloro-2-propanone;

aliphatic aldehydes, such as propanal; butanal; 2-methylbutanal; 3-methylbutanal; pentanal; methoxyethanal or ethoxyethanal;

chlorinated aliphatic aldehydes, such as chloroethanal; dichloroethanal; 2-chloropropanal or 2-chloro-2-methylpropanal;

aliphatic alcohols, such as methanol; ethanol; isopropanol; n-propanol, n-butanol; isobutanol or tert-butanol.

Among the solvents advantageously used in the process according to the invention, the aliphatic ethers, chlorinated aliphatic ethers, aliphatic ketones and chlorinated aliphatic ketones are more particularly preferred.

Among these preferred solvents, aliphatic ethers, especially those which are not miscible, or which are only slightly miscible with water, are even more preferred.

The amount of organic solvent used may vary over very wide limits.

The lower limit is established by the solubility of para-hydroxybenzoic acid in the solvent at the temperature at which the reaction is carried out.

The upper limit is generally non-critical, but it will be appreciated that, from an economic point of view, it is not profitable to operate at very low final concentrations of para-hydroxybenzoic acid in the solvent Additionally, when the organic solvent is miscible with water, it is essential that the final concentration of para-hydroxybenzoic acid in the solvent be adequate, such that a separation occurs between the aqueous layer containing the inorganic potassium salt formed and an essentially organic layer containing the para-hydroxybenzoic acid.

For these reasons, the amount of solvent used is such that the final para-hydroxybenzoic acid concentration in said solvent is generally at least equal to 8% by weight.

The temperature at which the process according to the invention is carried out is not very critical. It usually ranges from 10° C. to the boiling point of the organic solvent used.

However, as far as possible, it is preferred to avoid very low temperatures which may give rise to a crystallization of the inorganic potassium salt formed, and especially of potassium sulfate, or also very high temperatures, at which the solubility of the para-hydroxybenzoic acid in water is increased.

Accordingly, the reaction is preferably carried out at temperatures of from 40° C. to 80° C., this range not being critical.

The amount of strong inorganic acid and, more particularly, of sulfuric acid used is generally slightly greater than the amount theoretically required to release the para-hydroxybenzoic acid and the salicylic and 4-hydroxyisophthalic acid from their respective potassium salts.

This excess, which is often approximately 5% to 10% of the stoichiometric amount, enables the reaction to be completed more rapidly.

The sulfuric acid is advantageously introduced in the form of an aqueous solution, such as those commercially available; aqueous solutions which have a concentration of 60% to 98% by weight are most frequently used.

In practice, the process according to the present invention may be carried out as follows:

(i) An organic solvent as defined above, in an amount sufficient to dissolve the para-hydroxybenzoic acid corresponding to the potassium salts used, is added to the aqueous solution containing the dipotassium and/or the monopotassium salt of para-hydroxybenzoic acid at a concentration of 20 to 45% by weight and, where appropriate, the potassium salts of the other acids;

(ii) Depending upon the conditions, a homogeneous phase or two liquid phases are obtained, the latter case representing a preferred embodiment of the process of the invention;

(iii) Sulfuric acid is then added, under stirring, in an amount representing approximately 105% to 110% of the amount theoretically required (theory being 1 mole of pure $H_2SO_4$ for 1 mole of the dipotassium salt of para-hydroxybenzoic acid or of salicylic acid, 0.5 mole of $H_2SO_4$ for 1 mole of monopotassium salt of the para-hydroxybenzoic acid or of salicylic acid, and 1 mole of $H_2SO_4$ for 1 mole of potassium 4-hydroxyisophthalate);

(iv) The temperature is adjusted to the required value.

When the reaction is complete, two liquid phases are obtained:

(a) an aqueous phase containing practically all of the potassium sulfate formed;

(b) an essentially organic phase containing almost all of the para-hydroxybenzoic acid formed.

In fact:

either, and this constitutes the preferred embodiment, a solvent which is immiscible with water and consequently settles, has been employed;

or a solvent miscible with water has been employed, and separation occurs between the aqueous phase containing potassium sulfate and the organic phase containing the para-hydroxybenzoic acid.

The separation of these two phases is then carried out by decantation. The aqueous phase generally contains more than 10% by weight of potassium sulfate (which may, if required, be recovered) and generally less than 1% by weight of para-hydroxybenzoic acid.

The essentially organic phase is then treated in a manner known, per se, in order to separate the para-hydroxybenzoic acid.

For example, if the intended applications do not require a much greater purity than that obtained in the usual processes for the separation of para-hydroxybenzoic acid, an atomization of the said organic phase, that is, spraying it through a nozzle at a temperature which permits the instantaneous vaporization of the solvent may be carried out. This process is simple and provides a para-hydroxybenzoic acid of a purity at least comparable to that obtained by the processes of the prior art.

It is also possible to carry out a distillation of the organic solvent, followed by a cooling and a crystallization of the para-hydroxybenzoic acid by the addition of water, this typically being the preferred embodiment.

The para-hydroxybenzoic acid obtained according to this latter embodiment has a very low potassium sulfate content, generally less than 0.002% by weight and a salicylic acid and 4-hydroxyisophthalic acid content less than 0.02%.

Such a para-hydroxybenzoic acid may be used for the most stringent of applications in the food industry.

Additionally, it is observed that the para-hydroxybenzoic acid crystals thus prepared have a particle size which may be controlled during the crystallization by adjusting the temperature at which this operation is carried out. Thicker needles and a higher bulk density, resulting in a clear improvement in the flowability of the para-hydroxybenzoic acid, are obtained.

The process of the invention may be carried out in a discontinuous or continuous manner. It can easily be carried out within the context of the usual processes for the preparation of para-hydroxybenzoic acid from potassium phenate.

In order to further illustrate the present invention and the advantages thereof, the following specific example is given, it being understood that same is intended only as illustrative and in nowise limitative.

EXAMPLE

The following materials were charged into a 2000-cm$^3$ glass reactor, equipped with an efficient stirrer:
(i) 1445 g of an aqueous solution, at a strength of 16% by weight, of the dipotassium salt of para-hydroxybenzoic acid, containing 1 mole % of potassium salicylate relative to the dipotassium salt of para-hydroxybenzoic acid,
(ii) 743 g of methyl tert-butyl ether.

The contents of the reactor were stirred and 166 g of a 71% strength by weight aqueous solution of sulfuric acid (1.20 mole of $H_2SO_4$) were added: the pH of the aqueous phase was then approximately 2.

Stirring was continued for 30 minutes, increasing the temperature to 40° C. at the same time.

The contents of the reactor were then allowed to settle for 30 minutes at approximately 40° C.; two phases were obtained:
(a) a lower aqueous phase,
(b) an upper organic phase.

The aqueous phase was drawn off, which was still at a temperature of about 40° C.

The organic phase contained:
(i) 705 g of methyl tert-butyl ether;
(ii) 42 g of water;
(iii) 126 g of para-hydroxybenzoic acid;
(iv) 1.4 g of salicylic acid;
(v) 0.01 g of potassium sulfate.

The organic phase was treated as follows:
the methyl tert-butyl ether was distilled, while maintaining the volume of the phase constant by the gradual addition of water;
the distillation was terminated when the temperature of the condenser reached 98°–100° C.

A new aqueous phase containing para-hydroxybenzoic acid crystals in suspension was thus obtained.

This suspension was cooled from 100° C. to 85° C. over two hours, then from 85° C. to 40° C. over one hour.

The para-hydroxybenzoic acid which had crystallized was filtered at 40° C. The residue was washed with approximately 150 g of para-hydroxybenzoic acid; it was then dried.

120 g of para-hydroxybenzoic acid in the form of a crystallized white solid, having a good flowability, were obtained.

The para-hydroxybenzoic acid contained, as impurities:
(1) less than 0.001% of potassium sulfate;
(2) 0.012% of salicylic acid.

The isolation and purification yield of para-hydroxybenzoic acid relative to its dipotassium salt employed was approximately 80%. This yield can be improved, especially by decreasing the amounts of water used.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the recovery of purified para-hydroxybenzoic acid from an aqueous solution of dipotassium and/or monopotassium para-hydroxybenzoate, comprising (i) adding an organic solvent for para-hydroxybenzoic acid to such aqueous solution, in an amount sufficient to dissolve the para-hydroxybenzoic acid corresponding to said potassium salts thereof, (ii) next adding thereto a strong inorganic acid in an amount at least equal to a stoichiometric amount, relative to said dipotassium and/or monopotassium salt of para-hydroxybenzoic acid, and (iii) separating therefrom an essentially organic phase which comprises said para-hydroxybenzoic acid and an aqueous phase which comprises an inorganic potassium salt.

2. The process as defined by claim 1, further comprising crystallizing para-hydroxybenzoic acid from said organic phase.

3. The process as defined by claim 1, said strong inorganic acid comprising sulfuric acid.

4. The process as defined by claim 1, said organic solvent comprising an aliphatic ether, substituted aliphatic ether, aliphatic ketone, halogenated aliphatic ketone, aliphatic aldehyde or aliphatic alcohol.

5. The process as defined by claim 4, said organic solvent comprising an aliphatic ether, chlorinated aliphatic ether, aliphatic ketone or chlorinated aliphatic ketone.

6. The process as defined by claim 1, said organic solvent having a boiling point less than or equal to 120° C.

7. The process as defined by claim 1, said organic solvent comprising diisopropyl ether, methyl tert-butyl ether, ethyl isopropyl ether, ethyl propyl ether, butyl ethyl ether, ethyl isobutyl ether, ethyl tert-butyl ether, butyl methyl ether, isobutyl methyl ether, methyl pentyl ether, diethyl ether, dipropyl ether, isopropyl propyl ether, ethyl 1-propynyl ether, ethyl 2-propynyl ether, ethynyl propyl ether, allyl ethyl ether, allyl isopropyl ether, isopropyl vinyl ether, isobutyl vinyl ether, 2-bromoethyl ethyl ether, 2-chloroethyl ethyl ether, acetone, 2-butanone, 3-methyl-2-butanone, 3,3-dimethyl-2butanone, 2-pentanone, 3-pentanone, 3-chloro-2-butanone or 1-chloro-2-propanone.

8. The process as defined by claim 1, said organic solvent comprising an aliphatic ether immiscible or only slightly miscible with water.

9. The process as defined by claim 1, wherein the amount of organic solvent is such that the final para-hydroxybenzoic acid concentration in said solvent is at least equal to 8% by weight.

10. The process as defined by claim 1, carried out at a temperature of from 10° C. to the boiling point of said organic solvent.

11. The process as defined by claim 1, comprising adding from about 105% to 110% of the stoichiometric amount of sulfuric acid.

12. Essentially pure para-hydroxybenzoic acid containing less than 0.002% by weight of potassium sulfate and less than 0.02% by weight of salicylic acid and 4-hydroxyisophthalic acid.

* * * * *